US 6,551,288 B2

(12) United States Patent  
Payne et al.

(10) Patent No.: US 6,551,288 B2  
(45) Date of Patent: Apr. 22, 2003

(54) SAFETY-SHEATHED PHLEBOTOMY NEEDLE HOLDER

(75) Inventors: Timothy J. Payne, Santa Ana, CA (US); Jeffrey C. Smith, Newport Beach, CA (US)

(73) Assignee: Futura Medical Technologies, Inc., Solana Beach, CA (US)

( * ) Notice: Subject to any disclaimer, the term of this patent is extended or adjusted under 35 U.S.C. 154(b) by 0 days.

(21) Appl. No.: 10/086,997

(22) Filed: Feb. 28, 2002

(65) Prior Publication Data  
US 2002/0123721 A1 Sep. 5, 2002

Related U.S. Application Data  
(60) Provisional application No. 60/272,802, filed on Feb. 28, 2001.

(51) Int. Cl.$^7$ .................................................. A61M 5/00
(52) U.S. Cl. ................................................... 604/263
(58) Field of Search ................................. 604/263, 110, 604/164.08, 187, 192, 198

(56) References Cited

U.S. PATENT DOCUMENTS

| | | | | |
|---|---|---|---|---|
| 4,892,107 A | * | 1/1990 | Haber | 128/763 |
| 5,086,780 A | * | 2/1992 | Schmitt | 128/763 |
| 5,120,311 A | * | 6/1992 | Sagstetter et al. | 604/110 |
| 5,193,552 A | * | 3/1993 | Columbus et al. | 128/760 |
| 5,607,402 A | * | 3/1997 | Dufresne et al. | 604/263 |
| 5,709,669 A | * | 1/1998 | Haining | 604/232 |
| 5,746,215 A | * | 5/1998 | Manjarrez | 128/763 |
| 6,063,040 A | * | 5/2000 | Owen et al. | 600/573 |
| 6,152,901 A | * | 11/2000 | Arruego et al. | 604/195 |

* cited by examiner

Primary Examiner—Sharon Kennedy  
(74) Attorney, Agent, or Firm—Fulbright & Jaworski L.L.P.

(57) ABSTRACT

A safety-sheathed blood sampling needle for use with a standard vacutainer. The needle is housed in a protective hollow body and held in place with a non-tensioned elastic band. The needle may be extended outside the cover for use without removing the cover assembly from the needle, and may be locked into the use position with one hand. Moving the needle into the use position tensions the elastic band. After the sample is taken, the needle is unlocked and retracted back into the cover by the elastic band. Upon such retraction, the element used to extend the needle is either concealed or disconnected to prevent accidental reuse of the needle.

10 Claims, 8 Drawing Sheets

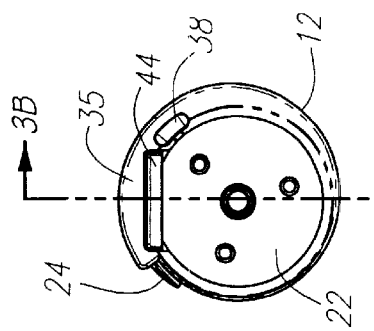
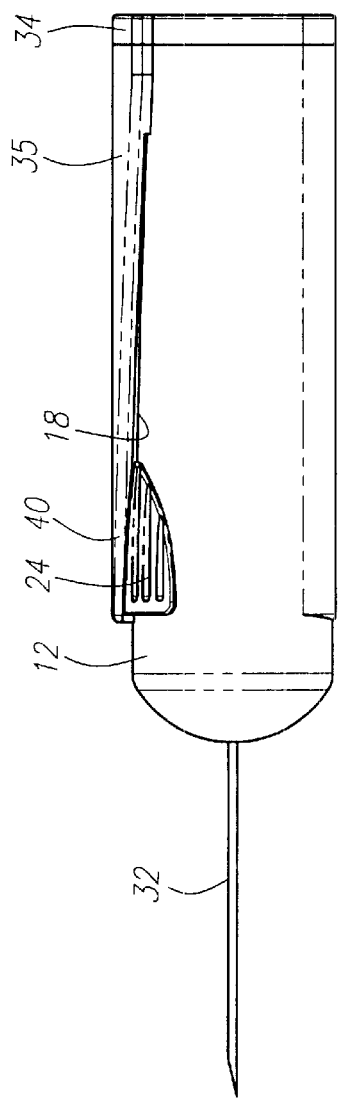
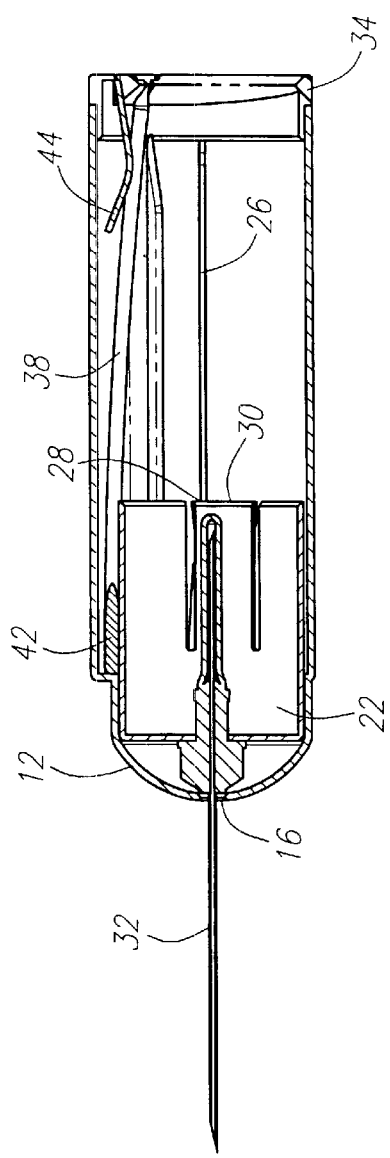

SAFETY-SHEATHED PHLEBOTOMY NEEDLE HOLDER

This is a utility application of Provisional Application Serial No. 60/272,802, filed Feb. 28, 2001.

BACKGROUND OF THE INVENTION

1. Field of the Invention

The field of the present invention is safety-sheathed needles.

2. Background of the Invention

The field of the present invention relates generally to apparatus and methods for protection against an accidental sharps injury or stick from an unprotected needle.

For some time, the art has recognized the desirability of protecting personnel from accidental sharps injuries or needle sticks. More recently, concerns have been expressed about the possibility of transmitting serious or potentially fatal infection as a result of such accidents. Most recently, legislation requiring the use of safe needle technology is pending in a number of States and before the Occupation Safety and Health Administration. Although the art has recognized the desirability of protecting against accidental sharps injuries or needle sticks, it is believed that practical protective devices are still not available, particularly for phlebotomy devices that utilize large containers that are not retained with the needle after the blood sample is obtained.

A typical blood collection container is a "vacutainer," which is essentially a short test tube with a hermetic seal at the open end, and containing a vacuum. To collect blood, the operator uses a phlebotomy needle with sharpened points on each end, inserts one end into a patient's vein, and inserts the other end through the vacutainer seal. The vacuum pulls blood into the vacutainer for a sterile blood sample. The vacutainer is then separated from the needle, and the vacutainer's seal closes tight enough to retain the liquid blood. But the needle has two sharp ends, and requires careful handling to avoid injury and the spread of blood-borne disease.

To help prevent needle injuries, European Patent No. 0 862 A1 discloses a device in which a needle is retracted into a syringe. In several of the embodiments, the device requires the user to independently operate a mechanical device to cause retraction of the needle. In the one embodiment that utilizes an elastic member, the elastic member is not pre-loaded and requires the user to depress the plunger to load the elastic member and thereafter continue to apply pressure on the plunger to avoid premature withdrawal of the plunger. As such, the device requires two hands for its operation.

Various methods of providing a preloaded retraction assembly which permit one hand operation are disclosed in co-owned PCT Application No. PCT/US97/20646, International Publication No. WO 98/20923. Although these devices operate successfully, the retraction member is in a tensioned, preloaded condition.

A final concern is the re-use of phlebotomy needles, which can cause disease transmission if the needles are not properly cleaned and sterilized between uses. Such re-use can be accidental if the technician is not careful to dispose of the needle after use.

Accordingly, there is a need for a sheathed phlebotomy needle that can be operated conveniently with one hand, stored in a non-tensioned condition, and constructed to minimize the opportunity for multiple uses.

SUMMARY OF THE INVENTION

The present invention is directed to improved sheathed needle phlebotomy (blood sampling) devices. A shuttle having a needle mounted thereto is retracted within a hollow body to safely store the needle. The hollow body has a generally longitudinally extending slot. A pusher element slides with the shuttle and extends through the slot for advance of the needle from the end of the hollow body. An interference element cooperates with the shuttle to retain the needle extended from the hollow body for use. A cap is positioned at one end of the hollow body to receive vacutainers.

In a first separate aspect of the present invention, an elastic band is coupled with the shuttle and the cap. This coupling allows for the band to be substantially unstressed before use, stretched upon needle deployment and operative to retract the needle upon activation.

In a second separate aspect of the present invention, the slot in the hollow body is facing tangentially of the body with the pusher element extending from the slot and movable through the slot circumferentially with rotation of the shuttle in the hollow body. This movement of the pusher element through the slot circumferentially can act to limit reuse.

In a third separate aspect of the present invention, the pusher element can be rotated to release the interference element. This allows automatic retraction of the shuttle under the influence of the elastic band.

In a fourth separate aspect of the present invention, a rotation impedance element may be used to prevent accidental rotation of the pusher element. This prevents accidental release of the interference element and retraction of the needle.

In a fifth separate aspect of the present invention, the pusher element can be disengaged from the shuttle to activate the needle retraction mechanism. This can act to limit reuse.

Accordingly, it is an object of the present invention to provide an improved safety cover for a phlebotomy needle. Other and further objects and advantages will appear hereafter.

BRIEF DESCRIPTION OF THE DRAWINGS

FIG. 3A is an exterior side view of a first embodiment of a sheathed phlebotomy needle holder in the use position.

FIG. 3B is an cross-section side view of a first embodiment of a sheathed phlebotomy needle holder in the use position.

FIG. 3C is an end view (from the vacutainer end) of a first embodiment of a sheathed phlebotomy needle holder in the use position, with the flap moved up out of the way for clarity.

DETAILED DESCRIPTION OF A PREFERRED EMBODIMENT

Figure 1:
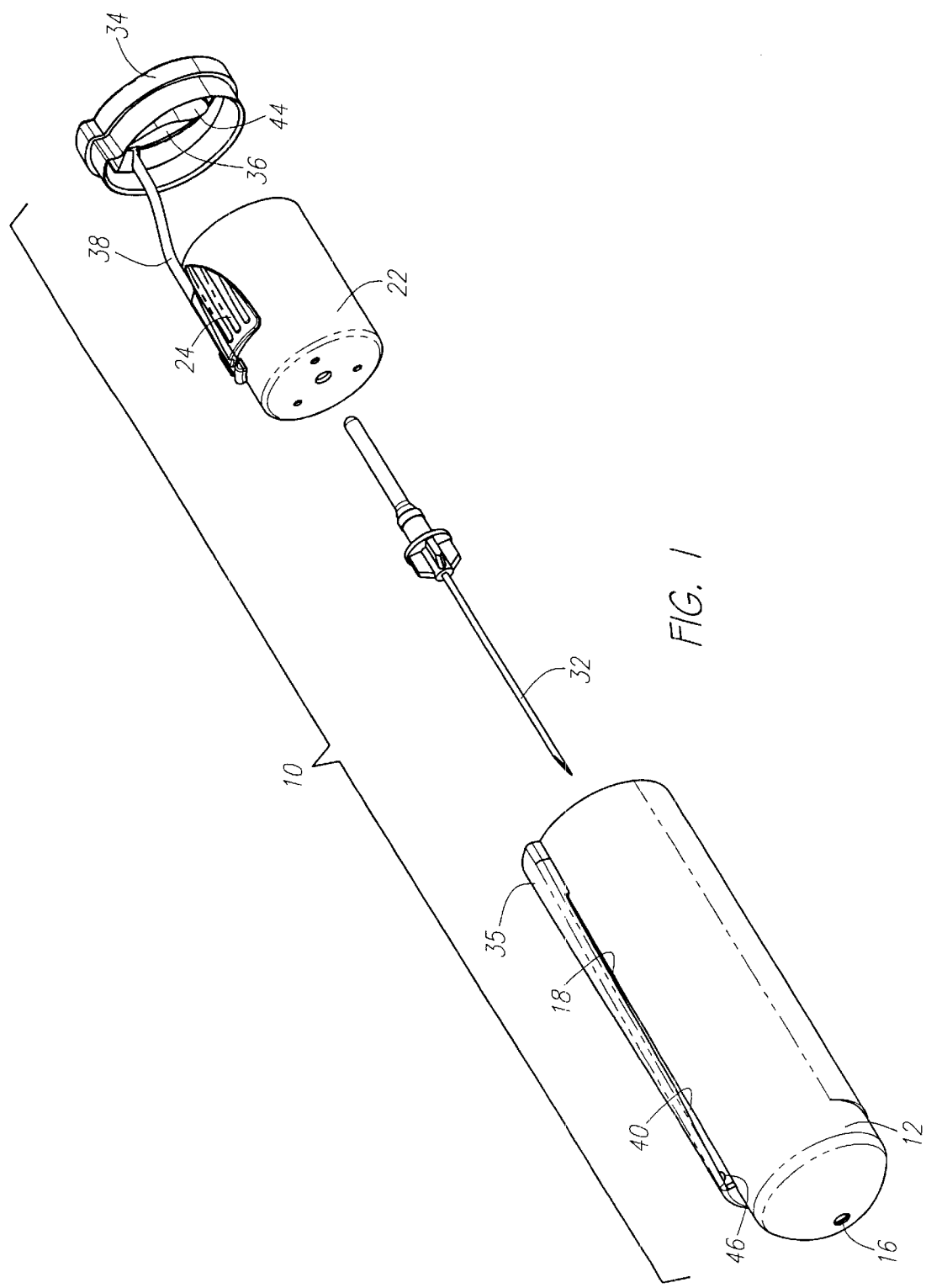
FIG. 1 is an exploded oblique view of a first embodiment of a sheathed phlebotomy needle holder.

As shown in FIG. 1, a preferred embodiment of a phlebotomy needle holder 10 may be comprised of substantially cylindrical hollow body 12 with an access port 14 in one end and a needle hole 16 at the other end, and a generally longitudinally extending slot 18. The access port 14 may be large enough to insert a vacutainer, and the needle hole 16 may be small enough to prevent fingers from entering the hollow body 12 and getting stuck by the phlebotomy needle 32. A shuttle 22 is slidable within the hollow body 12 and may have a pusher element 24 that extends through the slot 18. The pusher element may be accessed from the exterior of the hollow body 12 and slidable along the slot 18, which slides the shuttle 22 inside the hollow body 12. As shown in FIG. 3B, the hollow body 12 may have an interference element 26 and a stop end 28, the shuttle finger tab 30 of the shuttle 22 being able to slide along the interference element and engage the stop end 28 with the shuttle 22 advanced toward the needle hole 16. A phlebotomy needle 32 may be fixed to the shuttle 22 such that the longer end of the phlebotomy needle 32 (patient end) is pointing towards and aligned with the needle hole 16, and the shorter end of the phlebotomy needle 32 (vacutainer end) is pointing towards the access port 14, extending enough so that it can be used with a vacutainer.

All needles have a steeply angled bevel that forms the sharp tip of the needle, see FIG. 3A. In larger needles it may be desirable to orient the bevel to ease insertion. The phlebotomy needle 32 could be fixed to the shuttle in a preferred needle bevel orientation, or the phlebotomy needle 32 could be designed to rotate within the shuttle 22 so that the needle bevel orientation could be changed by the user.

Figure 5:
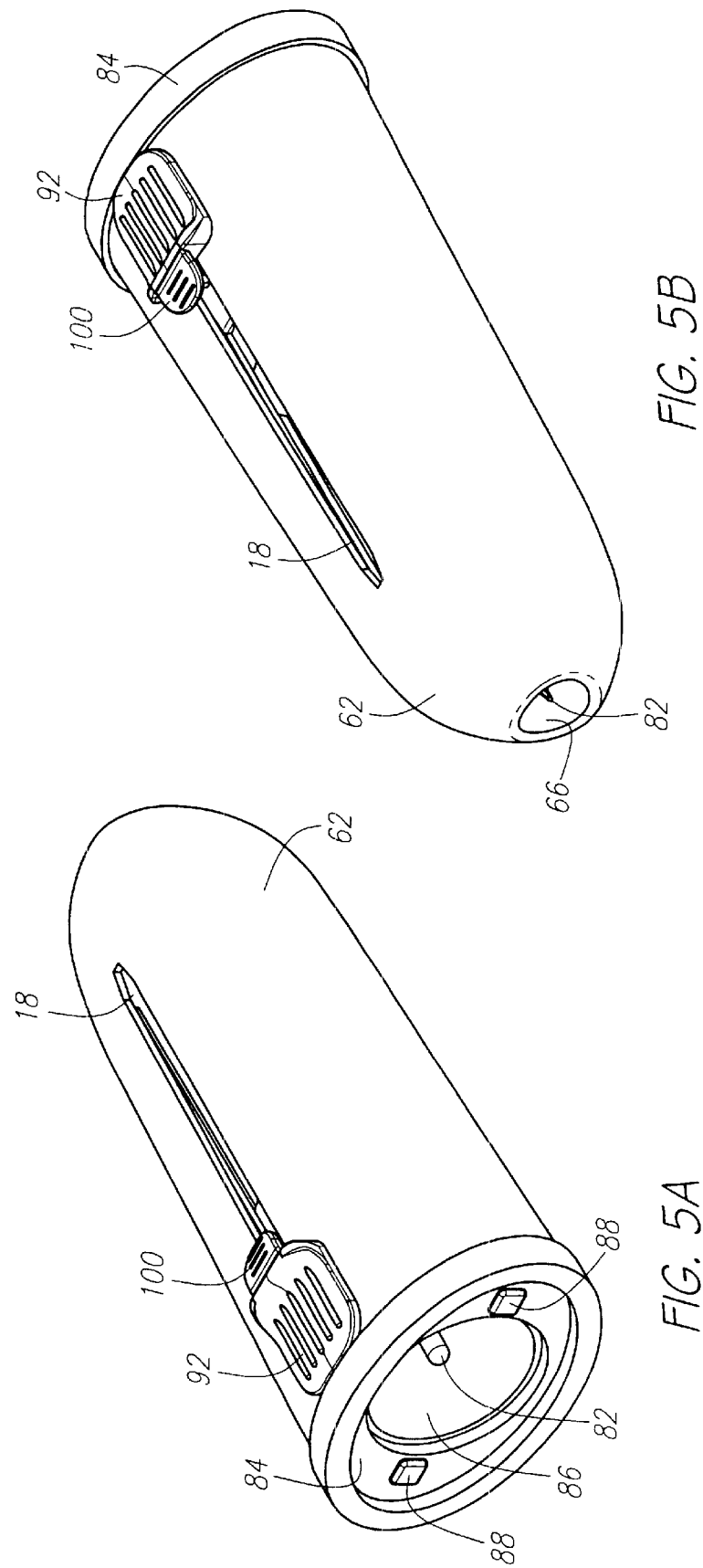
FIG. 5A is an oblique exterior view of the vacutainer end of a second embodiment of a sheathed phlebotomy needle holder in the shipped position.
FIG. 5B is an oblique exterior view of the needle end of a second embodiment of a sheathed phlebotomy needle holder in the shipped position.
Figure 6:
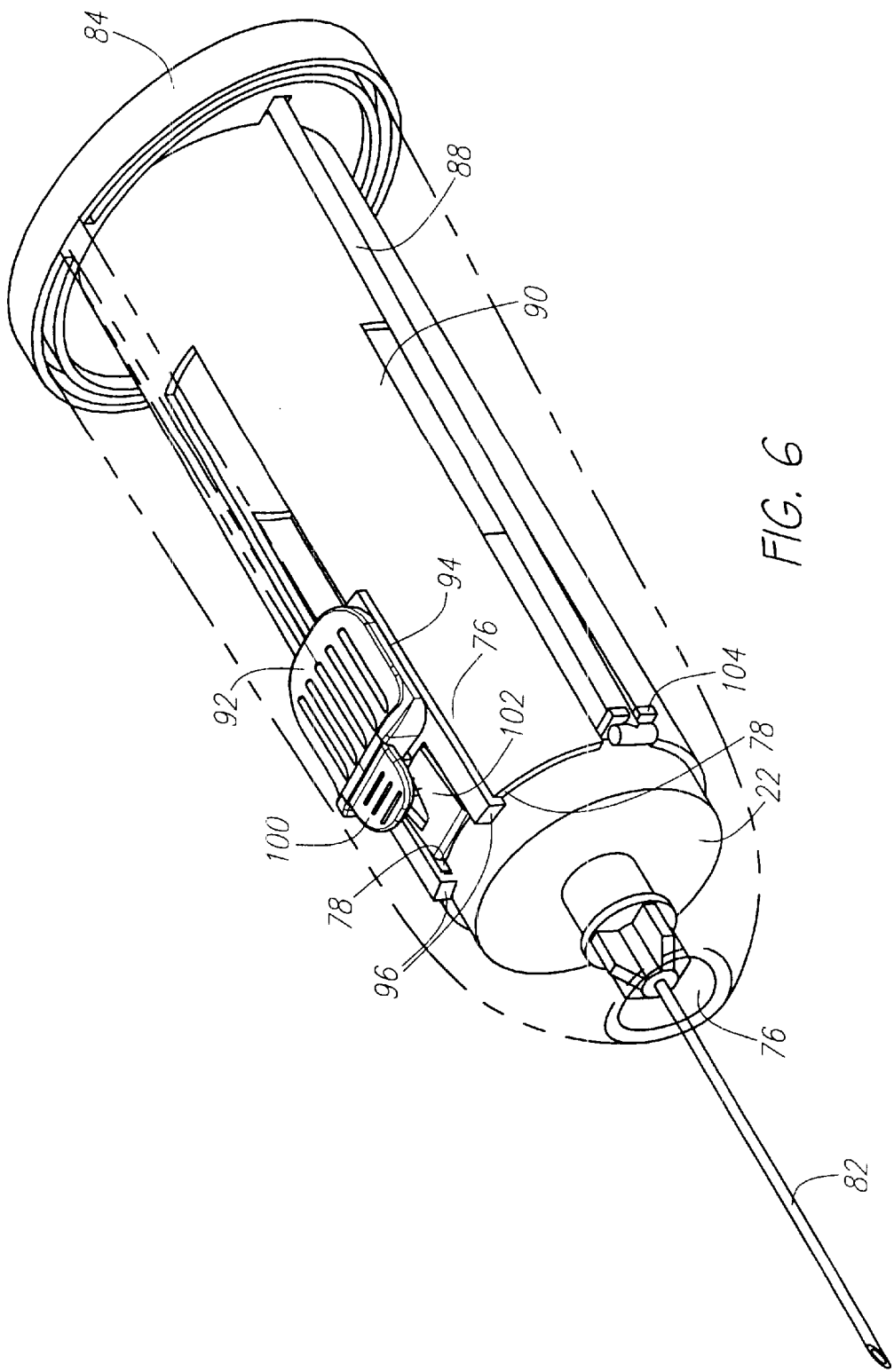
FIG. 6 is an oblique cut-away view of the needle end of a second embodiment of a sheathed phlebotomy needle holder in the use position.

As shown in FIGS. 5A and 6, a cap 34 may be positioned in the access port 14 and the cap 34 may include a vacutainer opening 36. An elastic band 38 may be coupled with the shuttle 22 and with the cap 34.

When the phlebotomy needle holder 10 is shipped, the shuttle 22 holding the phlebotomy needle 32 may be held in place towards the access port 14 by the elastic band 38, which is not tensioned or only slightly tensioned. To use, the operator may use his/her thumb to slide the exposed pusher element 24 towards the needle hole 16, which exposes the longer end of the phlebotomy needle 32 for insertion into the patient's vein. As shown in FIG. 3B, the needle 32 may be held in the use position by the shuttle finger tab 30, which slides along the interference element 26, essentially a rib on the inside of the hollow body 12, until it reaches the stop end 28 and drops down to hold the shuttle 22 in place. When the shuttle 22 is in the use position, the elastic band 38 may be stretched and provide tension on the shuttle 22. After the phlebotomy needle 32 is inserted into the vein, a vacutainer may be placed into the vacutainer opening 36, past the flap 44 (see below for description), and pushed onto the shorter end of the phlebotomy needle 32 to obtain the sample.

As shown in FIGS. 1—3A, the generally longitudinally extending slot 18 in the hollow body 12 may face tangentially to the body 12, and the pusher element 24 may extend about and be displaced from the side of the shuttle 22. The pusher element 24 may also have a base 42 fixed to the side of the shuttle 22. When the pusher element 24 is at the end of the slot adjacent the needle hole 40, where the slot 18 has a larger opening, the pusher element 24 may be circumferentially moved through the slot 18 when the shuttle 22 is rotated in the hollow body with the pusher element 24. If the pusher element 24 is rotated far enough, the shuttle finger tab 30 may rotate beyond the stop end 28 of the interference element 26, and the shuttle 22 may be retracted automatically by the tensioned elastic band 38. The pusher element 24 may slide back into a body channel 35 that is molded on the interior of the hollow body 12. After such retraction, the pusher element 24, along with the longer end of the phlebotomy needle 32, may be enclosed within the hollow body 12, and the shuttle 22 and phlebotomy needle 32 may not be easily extended for reuse.

Figure 2:
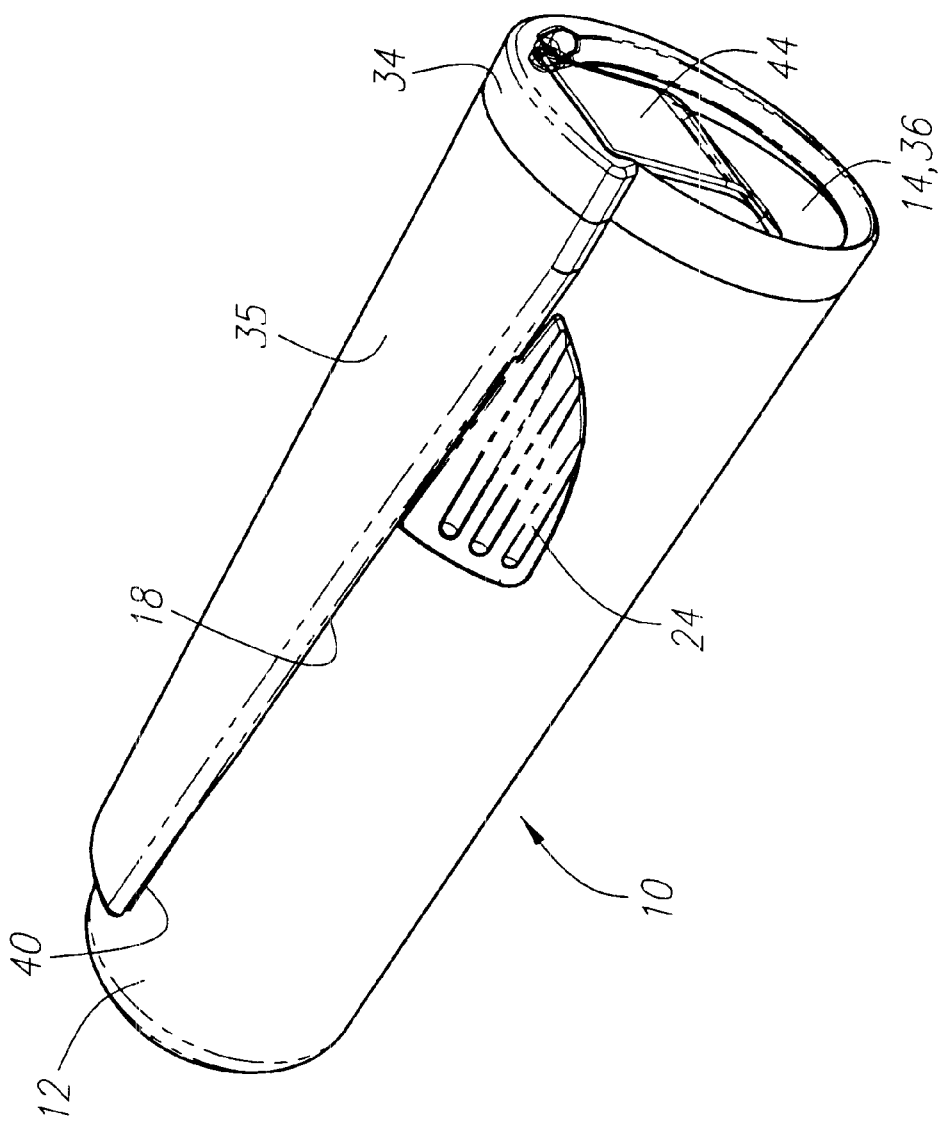
FIG. 2 is an exterior oblique view of the vacutainer end of a first embodiment of a sheathed phlebotomy needle holder in the shipped position.

As shown in FIGS. 2 and 3B, the cap 34 may further include a flap 44 hinged to one side of the access port and biased to extend across the access port. This flap 44 may prevent fingers from entering the access port and may protect the shorter end of the phlebotomy needle 32. The flap 44 may have a "living hinge" made of plastic that remembers its shape after removal of the vacutainer, or some other suitable structure that closes the flap when the vacutainer is removed. If desired, the flap could be arranged so that it automatically flips open when the phlebotomy needle holder 10 is moved into the use position, and to automatically flip down when retracted.

When manufacturing the phlebotomy needle holder 10, a special tool may be used to insert the shuttle 22 into the extended position along the body channel 35, such that the pusher element 24 is at the end of the slot adjacent the needle hole 40, and then rotated to expose the pusher element 24 outside the hollow body 12, and then slid back into the retracted shipping position. During manufacturing, the elastic band 38 attached to the shuttle 22 may have the other end hanging free, which end may then be attached to the cap 34, which may then be pressed into the hollow body 12, and may lock in place with a snap fit, friction fit or other suitable means, including sealant.

When the phlebotomy needle 32 is in the use position and being used, it may be desirable to prevent the shuttle 22 from accidentally rotating and retracting phlebotomy needle 32. As shown in FIG. 1, a preferred embodiment may have a hollow body 12 with a rotation impedance element 46 consisting of a resilient detent at the end of the slot adjacent the needle hole 40 to resist rotation of the pusher element 24 into the hollow body 12. There are numerous designs and locations for such a rotation impedance element, however, and it need not be a resilient detent nor located at the end of the slot adjacent the needle hole 40. For example, the finger tab 30 could have a sloped ramp that is engaged by the stop end 28, and would require a certain amount of force on the pusher element 24 to rotate the stop end 28 up that ramp. Or a detent could be placed on the shuttle finger tab 30 to prevent accidental rotation past the stop end 28. Alternatively, the elastic band 38 may provide sufficient tension between the shuttle finger tab 30 and the stop end 28 that a rotation impedance element 46 or similar device is not necessary to prevent accidental rotation of the shuttle 22.

As shown in FIG. 3B, the interference element 26 may be fixed to the hollow body 12. The shuttle finger tab 30 may slide along interference element 26 and drop down in place after it goes past the stop end 28. Any number of interference elements and stop ends could be used, however, such as a slot in the hollow body into which a finger tab drops down, with the finger tab having a ramp that allows the tab to be rotated out of the slot. There are innumerable configurations of the interference elements and stop ends, and the claims are not meant to be limited to the illustrated structures.

Figure 4:
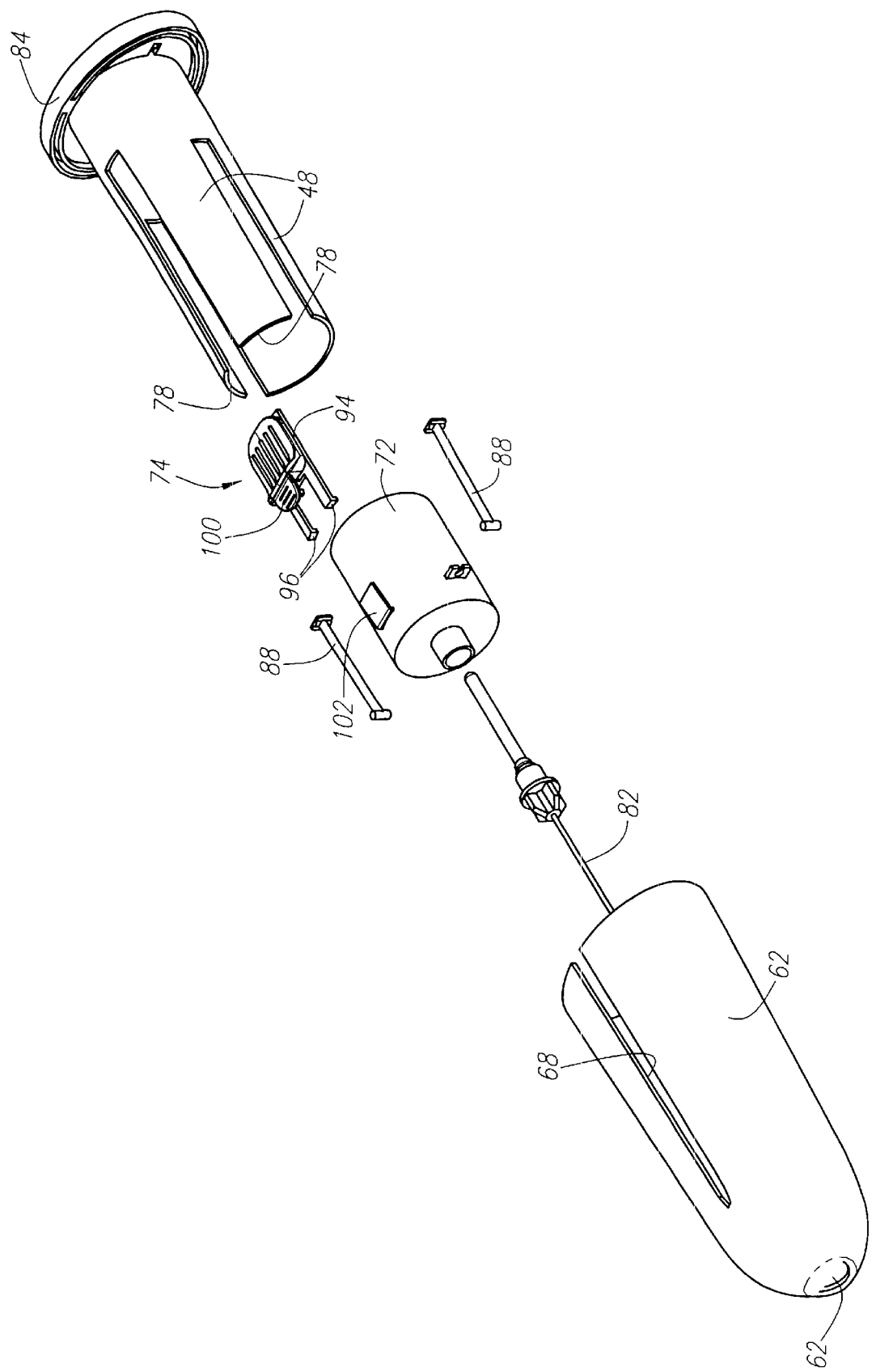
FIG. 4 is an exploded oblique view of a second embodiment of a sheathed phlebotomy needle holder.

As shown in FIG. 4, an alternative embodiment may similarly have a hollow body 62 with an access port 64 in one end and a needle hole 66 at the other end, and a generally longitudinally extending slot 68. The hollow body 62 may also have an interference element 76 that may include a guide 90 that extends into the hollow body 62 into which the shuttle 72 can slide. The guide 90 may have guideways to accommodate movement of the shuttle's release tab 102 and shuttle's elastic band attachment points 104. A shuttle 72 may have a pusher element 74 that may extend through the slot 68. The pusher element may be accessed from the exterior of the hollow body 62 and slid along the slot 68, which also slides the shuttle 72 inside the hollow body 62.

Figure 7:
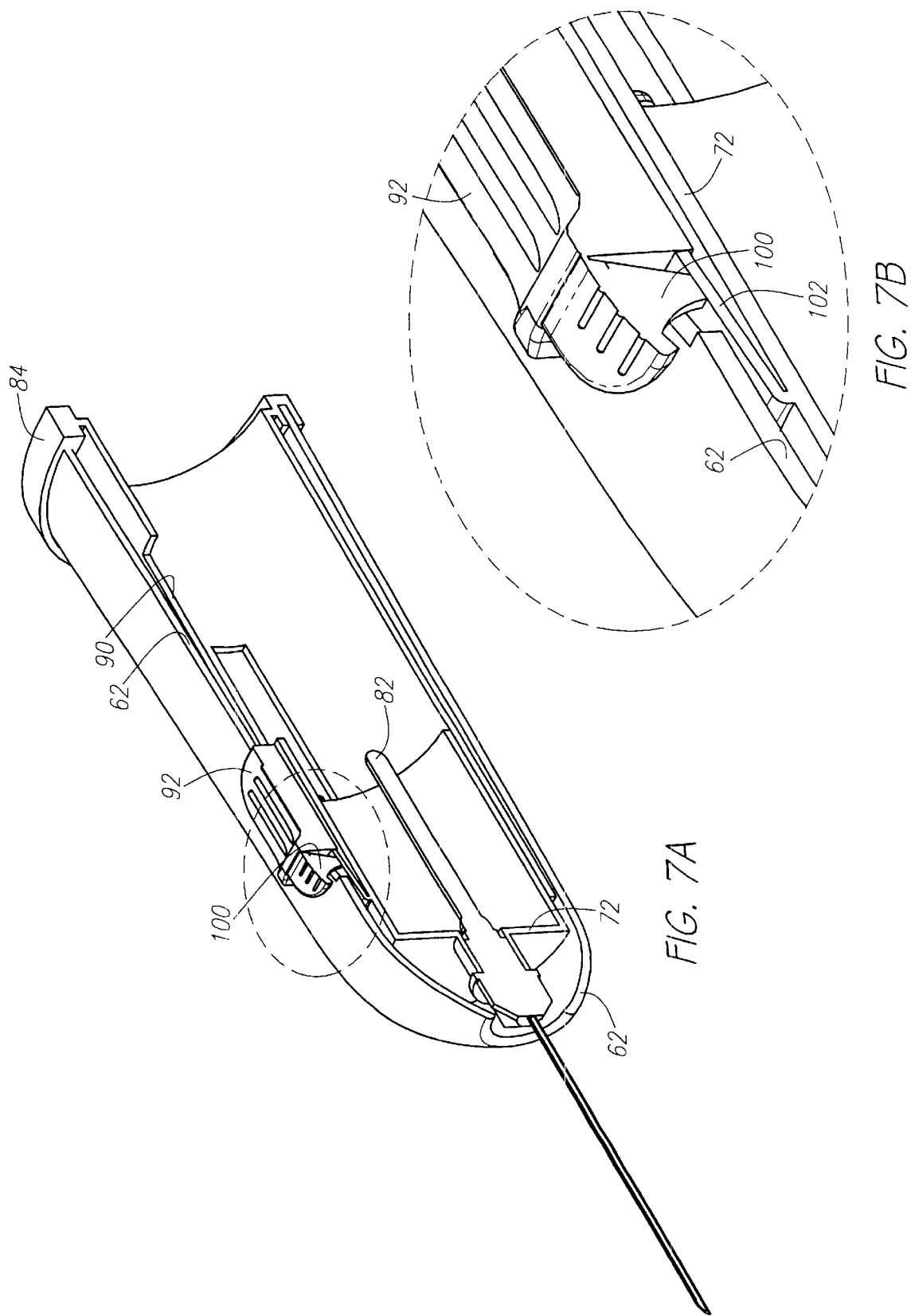
FIG. 7A is an oblique cross-section view of the needle end of a second embodiment of a sheathed phlebotomy needle holder in the use position.
FIG. 7B is a close-up of a section of FIG. 7A showing the detail of the trigger and shuttle release tab in the use position.

The pusher element 74 may include a thumb slider 92, a base 94 beneath the slot 68 with an engagement shoulder 96 comprised of two arms facing toward the needle hole 66. As shown in FIGS. 7A and 7B, the pusher element 74 may be connected with a trigger 100 located toward the engagement shoulder 96, the trigger 100 being capable of moving in a generally downward direction towards the interior of the hollow body 62. The shuttle 72 may be connected with a release tab 102, aligned with the base 94 beneath the trigger 100 and flexible toward the shuttle 72. As shown in FIG. 7B, the pusher element 74 may be removably engaged with the shuttle 72, held in place by the shuttle's release tab 102 and the tension created by two elastic bands 88 on opposite sides of the shuttle 72. Although two bands 88 are depicted in FIG. 4, more or less may be used. The cap 84 may include a vacutainer opening 86, and a protective flap (not shown). As shown in FIG. 5A, the shape of the hollow body may be an oval cylinder to accommodate the two elastic bands 88 and provide a comfortable grip for the user. Because the shuttle 72 need not rotate in this alternative embodiment, the hollow body 62, the guide 90 and the shuttle 72 need not be substantially cylindrical, and could be virtually any shape.

Figure 8:
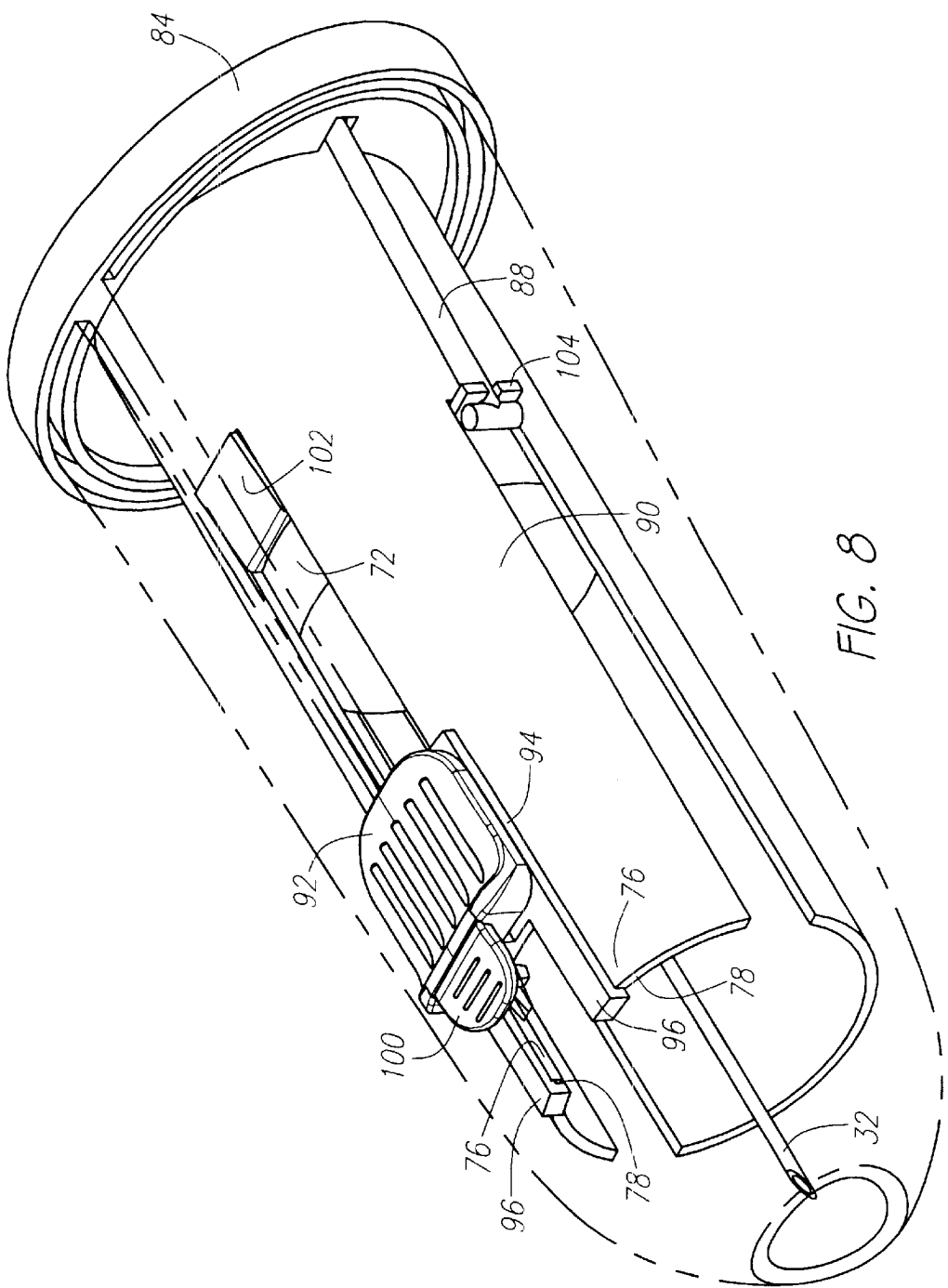
FIG. 8 is an oblique cut-away view of the needle end of a second embodiment of a sheathed phlebotomy needle holder in the retracted position.

In the shipped position, as shown in FIGS. 5A and 5B, the elastic bands 88 between the shuttle 72 and the cap 84 may be untensioned or slightly tensioned, holding the shuttle 72 and needle 82 in the retracted position. As shown in FIG. 6, the shuttle 72 and needle 82 may be moved into the use position by sliding the pusher element 74 with the operator's thumb, and at the full extension of needle 82 the two arms of the engagement shoulder 96 may engage the stop end 88 of the guide 90, locking the thumb slider 92 into place with the shuttle 72 advanced toward the needle hole 66 and the needle 82 exposed for use, as shown in FIGS. 7A and 7B. The operator may then insert the needle's 82 long end into the vein and push a vacutainer into the vacutainer opening to obtain the sample. To retract the shuttle 72 and needle 82 after use, the operator may press the trigger I 00, which depresses the release tab 102 of the shuttle 72, to disengage the shuttle 72 from the thumb slider 92, and the tensioned elastic bands retract the shuttle 72, while leaving the thumb slider 92 locked in position towards the needle hole 66, as shown in FIG. 8. Because the thumb slider 92 remains locked in the extended position while the shuttle is in the retracted position, this minimizes the potential for accidental reuse of the phlebotomy needle, and leaves the needle in a safe, retracted position.

What is claimed is:

1. A phlebotomy needle holder comprising
   a hollow body including an access port at one end, a needle hole at the other, a generally longitudinally extending slot in the body;
   a shuttle slidable within the hollow body;
   a pusher element extending through the slot and slidable along the slot with sliding of the shuttle within the hollow body;
   an interference element including a stop end, the shuttle being slidable along the interference element and engagable with the stop end with the shuttle advanced toward the needle hole;
   a phlebotomy needle fixed to and extending through the shuttle and aligned with the needle hole;
   a cap positioned in the access port and including a vacutainer opening;
   an elastic band coupled with the shuttle and with the cap.

2. A phlebotomy needle holder comprising
   a hollow body including an access port at one end, a needle hole at the other, a generally longitudinally extending slot in the body;
   a shuttle slidable within the hollow body;
   a pusher element extending through the slot and slidable along the slot with sliding of the shuttle within the hollow body;
   an interference element including a stop end, the shuttle being slidable along the interference element and engagable with the stop end with the shuttle advanced toward the needle hole;
   a phlebotomy needle fixed to and extending through the shuttle and aligned with the needle hole;
   a cap positioned in the access port and including a vacutainer opening;
   an elastic band coupled with the shuttle and with the cap, the generally longitudinally extending slot in the body facing tangentially of the body, the pusher element extending about and displaced from the side of the shuttle and having a base fixed to the side of the shuttle, the pusher element movable through the slot circumferentially with rotation of the shuttle in the hollow body with the pusher element at the end of the slot adjacent the needle hole.

3. The phlebotomy needle holder of claim 2, the cap further including a flap hinged to one side of the access port and biased to extend across the access port.

4. The phlebotomy needle holder of claim 2, the shuttle being disengagable from the stop end of the interference element when the pusher element is rotated.

5. The phlebotomy needle holder of claim 4, further comprising a rotation impedance element extending between the hollow body and the shuttle to resist rotation of the pusher element into the hollow body.

6. The phlebotomy needle holder of claim 5, the interference element being fixed to the hollow body.

7. The phlebotomy needle holder of claim 1, the interference element being fixed to the cap.

8. The phlebotomy needle holder of claim 7, the interference element including a guide extending in the hollow body and slidably receiving the shuttle.

9. A phlebotomy needle holder comprising
   a hollow body including an access port at one end, a needle hole at the other, a generally longitudinally extending slot in the body;
   a shuttle slidable within the hollow body;
   a pusher element extending through the slot and slidable along the slot with sliding of the shuttle within the hollow body;
   an interference element including a stop end, the shuttle being slidable along the interference element and engagable with the stop end with the shuttle advanced toward the needle hole;

a phlebotomy needle fixed to and extending through the shuttle and aligned with the needle hole;

a cap positioned in the access port and including a vacutainer opening;

an elastic band coupled with the shuttle and with the cap, the pusher element including a thumb slider, a base beneath the slot with an engagement shoulder facing toward the needle hole and connected with the thumb slider and a trigger movable on the thumb slider toward the engagement shoulder, the shuttle including a release tab connected with the shuttle, aligned with the base beneath the trigger and flexible toward the shuttle.

10. The phlebotomy needle holder of claim 1, there being two of said elastic band, the elastic bands being diametrically opposed to either side of the shuttle.

* * * * *